US012129459B2

(12) United States Patent
Chiu (10) Patent No.: US 12,129,459 B2
(45) Date of Patent: Oct. 29, 2024

(54) METHOD FOR USING AQUEOUS TWO-PHASE SYSTEM FOR THE ISOLATION, PURIFICATION AND/OR CONCENTRATION OF SHORT NUCLEIC ACID FRAGMENTS

(71) Applicant: Phase Scientific International, Ltd., Hong Kong (CN)

(72) Inventor: Yin To Chiu, Hong Kong (CN)

(73) Assignee: PHASE SCIENTIFIC INTERNATIONAL, LTD., Hong Kong (CN)

( * ) Notice: Subject to any disclaimer, the term of this patent is extended or adjusted under 35 U.S.C. 154(b) by 38 days.

(21) Appl. No.: 18/318,711

(22) Filed: May 16, 2023

(65) Prior Publication Data

US 2023/0287385 A1    Sep. 14, 2023

Related U.S. Application Data

(62) Division of application No. 16/646,582, filed as application No. PCT/US2018/051354 on Sep. 17, 2018, now abandoned.

(60) Provisional application No. 62/560,180, filed on Sep. 18, 2017.

(51) Int. Cl.
*C12N 15/10* (2006.01)
*C07H 21/04* (2006.01)

(52) U.S. Cl.
CPC ......... *C12N 15/1006* (2013.01); *C07H 21/04* (2013.01)

(58) Field of Classification Search
CPC . C07H 21/04; C12N 15/1003; C12N 15/1006
See application file for complete search history.

(56) References Cited

U.S. PATENT DOCUMENTS

| | | | |
|---|---|---|---|
| 6,132,763 A | 10/2000 | Fisher | |
| 6,399,385 B1 | 6/2002 | Croyle et al. | |
| 7,626,017 B2 | 12/2009 | Laugharn, Jr. | |
| 7,666,583 B2 | 2/2010 | Mor et al. | |
| 7,803,405 B2 | 9/2010 | Keating et al. | |
| 9,823,247 B2 | 11/2017 | Kamei et al. | |
| 10,006,911 B2 | 6/2018 | Kamei et al. | |
| 10,359,423 B2 | 7/2019 | Kamei et al. | |
| 10,578,616 B2 | 3/2020 | Kamei et al. | |
| 11,287,426 B2 | 3/2022 | Kamei et al. | |
| 11,327,075 B2 | 5/2022 | Kamei et al. | |
| 2002/0042506 A1 | 4/2002 | Kristyanne et al. | |
| 2005/0077497 A1 | 4/2005 | Anderson | |
| 2006/0025579 A1 | 2/2006 | Riedl et al. | |
| 2006/0166349 A1 | 7/2006 | Kepka et al. | |
| 2007/0161000 A1 | 7/2007 | Van Alstine et al. | |
| 2008/0242825 A1 | 10/2008 | Devi et al. | |
| 2009/0192111 A1 | 7/2009 | Bader et al. | |
| 2009/0286966 A1 | 11/2009 | Christensen et al. | |
| 2010/0174052 A1 | 7/2010 | Hjorth et al. | |
| 2010/0179252 A1 | 7/2010 | Johansson et al. | |
| 2011/0257378 A1 | 10/2011 | Tran et al. | |
| 2011/0263040 A1 | 10/2011 | Jones | |
| 2013/0164825 A1 | 6/2013 | Christoffel et al. | |
| 2014/0121357 A1 | 5/2014 | Segura Ruiz et al. | |
| 2014/0221549 A1 | 8/2014 | Bodkhe et al. | |
| 2014/0227712 A1 | 8/2014 | Horlitz et al. | |
| 2014/0228549 A1 | 8/2014 | Bernhard et al. | |
| 2015/0166592 A1 | 6/2015 | Guo | |
| 2015/0253320 A1 | 9/2015 | Kamei et al. | |
| 2018/0100854 A1 | 4/2018 | Kamei et al. | |
| 2018/0258419 A1 | 9/2018 | Fischer et al. | |
| 2018/0259521 A1 | 9/2018 | Kamei et al. | |
| 2019/0033308 A1 | 1/2019 | Kamei et al. | |
| 2019/0187140 A1 | 6/2019 | Kamei et al. | |
| 2019/0250156 A1 | 8/2019 | Kamei et al. | |
| 2019/0391143 A1 | 12/2019 | Kamei et al. | |
| 2020/0150116 A1 | 5/2020 | Kamei et al. | |
| 2020/0284791 A1 | 9/2020 | Kamei et al. | |
| 2022/0252598 A1 | 8/2022 | Kamei et al. | |

FOREIGN PATENT DOCUMENTS

| | | |
|---|---|---|
| CN | 101679481 A | 3/2010 |
| CN | 101835790 A | 9/2010 |
| CN | 102264901 A | 11/2011 |
| CN | 102272144 A | 12/2011 |
| CN | 102421898 A | 4/2012 |

(Continued)

OTHER PUBLICATIONS

Matos et al., Separation and Purification Technology, 2014, 122, p. 144-148. (Year: 2014).*
Ivanenko et al., "Synthesis of pharmacologically active hydrogels based on combined silicon and titanium polyolates", Russian Chemical Bulletin, International Edition, 2012, 61(11), pp. 2163-2171.
Gu et al., "Effect of particle size in a colloidal hydrogel scaffold for 3D cell culture", Colloids and Surfaces B: Biointerfaces, 2015, 136, p. 1139-1147.
Radi, B., "Reinforced hydrogels for silicone copolymer delivery for scar remediation", 2010, PhD thesis, Queensland University of Technology, 255 pages.

(Continued)

*Primary Examiner* — Jonathan S Lau
(74) *Attorney, Agent, or Firm* — EAGLE IP LIMITED (57) ABSTRACT

The present invention relates to methods of using aqueous two-phase system (ATPS) for the isolation, concentration and/or purification of short nucleic acid fragment having about or less than 250 base pairs (bp). In one embodiment, the present invention provides a composition and kit for the purification of short nucleic acid fragments having about or less than 250 base pairs from nucleic acid-containing biological materials. In another embodiment, the present invention provides uses of certain salts and/or polymers in a two-phase system for the purification of short nucleic acid fragments having about or less than 250 base pairs from nucleic acid containing biological materials.

13 Claims, 3 Drawing Sheets

(56) References Cited

FOREIGN PATENT DOCUMENTS

| | | |
|---|---|---|
| CN | 103476786 A | 12/2013 |
| CN | 103797023 A | 5/2014 |
| CN | 104707358 A | 6/2015 |
| CN | 106662582 A | 5/2017 |
| CN | 108342383 A | 7/2018 |
| CN | 110003323 A | 7/2019 |
| EP | 0268946 A2 | 6/1988 |
| JP | 2000245460 A | 9/2000 |
| JP | 2002537106 A | 11/2002 |
| JP | 2007525222 A | 9/2007 |
| JP | 2017513015 A | 5/2017 |
| WO | 0050161 A1 | 8/2000 |
| WO | 2002057289 A1 | 7/2002 |
| WO | 2007140417 A2 | 12/2007 |
| WO | 2011159537 A2 | 12/2011 |
| WO | 2014128129 A1 | 8/2014 |
| WO | 2015134938 A1 | 9/2015 |
| WO | 2016155888 A1 | 10/2016 |
| WO | 2017041030 A1 | 3/2017 |
| WO | 2017214315 A1 | 12/2017 |
| WO | 2018039139 A1 | 3/2018 |
| WO | 2018183454 A1 | 10/2018 |
| WO | 2018183465 A1 | 10/2018 |
| WO | 2018222972 A1 | 12/2018 |
| WO | 2019046553 A1 | 3/2019 |
| WO | 2019046563 A1 | 3/2019 |
| WO | 2019055926 A2 | 3/2019 |
| WO | 2019118705 A1 | 6/2019 |
| WO | 2019118712 A1 | 6/2019 |
| WO | 2019143895 A1 | 7/2019 |
| WO | 2019143943 A2 | 7/2019 |
| WO | 2019144016 A1 | 7/2019 |
| WO | 2019144030 A1 | 7/2019 |
| WO | 2021037075 A1 | 3/2021 |
| WO | 2021148393 A1 | 7/2021 |
| WO | 2021185336 A1 | 9/2021 |
| WO | 2022008591 A1 | 1/2022 |

OTHER PUBLICATIONS

Khonani et al., "Synthesis of hydrogels based on silicon polyolates", Russian Chemical Bulletin, International Edition, 2010, 59(1), pp. 75-80.

Shin Hyunwoo et al., "Aqueous two-phase system to isolate extracellular vesicles from urine for prostate cancer diagnosis", PLoS One, vol. 13, No. 3, Mar. 27, 2018 (Mar. 27, 2018), p. 0194818.

Pereira Matheus M. et al., "Pre-treatment strategies based on aqueous two-phase systems comprising ionic liquids to improve the adrenal cancer diagnosis", Journal of Molecular Liquids, vol. 367, Sep. 22, 2022, p. 120409, XP093103949.

Mendes Maria S. M. et al., "Aqueous two-phase systems as multipurpose tools to improve biomarker analysis", Separation and Purification Technology, vol. 317, Apr. 17, 2023 (Apr. 17, 2023), p. 123875, XP093103947.

Lee, Hoyoon, et al., "Precision cell-free DNA extraction for liquid biopsy by integrated microfluidics." NPJ precision oncology 4.1 (2020): 3.

Ahmed et al., "Aqueous Two-Phase Systems and Microfluidics for Microscale Assays and Analytical Measurements", Annual Review of Analytical Chemistry, 2021 14:1, 231-255.

Filip Janku; et al., "A novel method for liquid-phase extraction of cell-free DNA for detection of circulating tumor DNA", Scientific reports, 2021, 11(1): 19653.

Luechau, Frank; et al. (2009) Primary capture of high molecular weight nucleic acids using aqueous two-phase systems. Separation and purification technology, 66.1: 202-207.

Nazer, Behzad; et al. (2017) Plasmid DNA affinity partitioning using polyethylene glycol-sodium sulfate aqueous two-phase systems. Journal of Chromatography B, 1044: 112-119.

Sorber L, et al. (2017) A Comparison of Cell-Free DNA Isolation Kits: Isolation and Quantification of Cell-Free DNA in Plasma. J Mol Diagn. Jan;19(1):162-168.

Frank Luechau, et al., Partition of plasmid DNA in polymer-salt aqueous two-phase systems, Separation and Purification Technology, Apr. 20, 2009, pp. 397-404, vol. 66, No. 2, Elsevier Science, Amsterdam, NL.

Vijayaragavan K. Saagar et al., Separation of porcine parvovirus from bovine serum albumin using PEG-salt aqueous two-phase system, Journal of Chromatography B, Sep. 1, 2014, pp. 118-126, vol. 967, NL.

Erik Jue et al., Using an aqueous two-phase polymer-salt system to rapidly concentrate viruses for improving the detection limit of the lateral-flow immunoassay: Concentrating Viruses in a Polymer-Salt System, Biotechnology and Bioengineering, Dec. 1, 2014, pp. 2499-2507, vol. 111, No. 12, US.

Paz Sean et al., A simplified SARS-COV-2 detection protocol for research laboratories, PLoS One, Dec. 18, 2020, p. e0244271, vol. 15, No. 12.

Steven B. Zimmerman and Lizabeth D. Murphy, Excluded Volume Effects on the Partition of Single- and Double-Stranded Oligodeoxynucleotides Between Two Liquid Phases, Biopolymers, Oct. 1992, 1365-1373, vol. 32, Issue 10, John Wiley & Sons, Inc.

Steven B. Zimmerman and Stefan O. Trach, Excluded Volume Effects on the Partition of Macromolecules Between Two Liquid Phases, Biopolymers, 1990, 703-718, vol. 30, Issue 7-8, John Wiley & Sons, Inc.

T.Matos, et. al., Isolation of PCR DNA fragments using aqueous two-phase systems, Separation and Purification Technology, Feb. 10, 2014, 144-148, vol. 122, Elsevier B.V.

Andreas Frerix, et. al., Exploitation of the Coil-Globule Plasmid DNA Transition Induced by Small Changes in Temperature, pH Salt, and Poly(ethylene glycol) Compositions for Directed Partitioning in Aqueous Two-Phase Systems, Langmuir, Mar. 25, 2006, 4282-4290, vol. 22 Issue 9, American Chemical Society.

Ricky Y. T. Chiu, et al., An Aqueous Two-Phase System for the Concentration and Extraction of Proteins from the Interface for Detection Using the Lateral-Flow Immunoassay, PLoS One, Nov. 10, 2015, 1-14, PLOS, California, US.

K. Jessie, et al., Protein Precipitation Method for Salivary Proteins and Rehydration Buffer for Two-Dimensional Electrophoresis, Biotechnology, 2008, 686-693, 7 (4), Asian Network for Scientific Information.

Richard J. Wicks, et al., The extraction and purification of DNA labelled with [methyl-3 H]thymidine in aquatic bacterial production studies, Journal of Plankton Research, 1987, 1159-1166, vol. 9 no. 6, IRL Press Limited, Oxford, England.

Donald C Rio, et al., Purification of RNA by SDS solubilization and phenol extraction, Cold Spring Harb Protoc, Jun. 2010, 1-4, vol. 2010 Issue 6, Cold Spring Harbor Laboratory Press, NY, USA.

Zsolt Czimmerer, et al., A Versatile Method to Design Stem-Loop Primer-Based Quantitative PCR Assays for Detecting Small Regulatory RNA Molecules, PLOS ONE, Jan. 31, 2013, 1-10, vol. 8 Issue 1, PLoS, California, U.

Wu et al., "Factors Affecting Aqueous Two-Phase Extraction", Biopharmaceutical Technology (Fourth Edition), Aug. 2015, p. 122-126, China medicine science and technology press.

"Silicone Polyethers—Silsurf", Retrieved from the internet <URL: https://www.siltech.com/products/silicone-polyethers-silsurf/#:~:text=Silicone%20polyethers%2C%20or%20silicone%20surfactants,specific%20properties%20of%20a%20product>. [retrieved on Feb. 17, 2023].

Fei Yu, et al., "Comparative Evaluation of Three Preprocessing Methods for Extraction and Detection of Influenza A Virus Nucleic Acids from Sputum", Front Med (Lausanne), 2018 year, vol. 5:56.

Piotr Chomczynski, et al., "The single-step method of RNA isolation by acid guanidinium thiocyanate-phenol-chloroform extraction: twenty-something years on", Nature Protocols, 2006, 1(2), 581-585.

Ziegler Ys, et al. (2014) Plasma membrane proteomics of human breast cancer cell lines identifies potential targets for breast cancer diagnosis and treatment. PLoS One. 9(7):e102341.

Schindler J, et al. (2008) Aqueous polymer two-phase systems for the proteomic analysis of plasma membranes from minute brain samples. J Proteome Res 7(1):432-442.

(56) References Cited

OTHER PUBLICATIONS

Spindler KL, et al. (2015) Circulating free DNA as biomarker and source for mutation detection in metastatic colorectal cancer. PLoS One. 10(4):e0108247.

Riedl W, et al. (2008) Membrane-supported extraction of biomolecules with aqueous two-phase systems[J]. Desalination, 224(1-3): 160-167.

Frerix A, et al. (2005) Scalable recovery of plasmid DNA based on aqueous two-phase separation. Biotechnol Appl Biochem. 42(Pt 1):57-66.

Crucho Cic, et al. (2017) Polymeric nanoparticles: A study on the preparation variables and characterization methods. Mater Sci Eng C Mater Biol Appl. 80:771-784.

Shin H, et al. (2015) High-yield isolation of extracellular vesicles using aqueous two-phase system. Sci Rep. 5:13103.

Zeringer E, et al. (2015) Strategies for isolation of exosomes. Cold Spring Harb Protoc. (4):319-323.

Iqbal M, et al. (2016) Aqueous two-phase system (ATPS): an overview and advances in its applications. Biol Proced Online. 18:18.

Zhou et al. (2015) Nanoparticle Vesicles with Controllable Surface Topographies through Block Copolymer-Mediated Self-Assembly of Silica Nanospheres, Langmuir, vol. 31(48), 11 pp. 13214-13220.

Bashir et al. (2016) Controlled-release of Bacillus thurigiensis formulations encapsulated in light-resistant colloidosomal micro-capsules for the management of lepidopteran pests of *Brassica* crops, PEERJ., vol. 4(e2524). pp. 1-14.
Sigma-Aldrich "Poly(ethylene glycol) octyl ether" Retrieved from the Internet <URL:https://www.google.com/search?q=poly%28ethylene+glycol%29+octyl+ether&source=Int&tbs=cdr%3A1%2Ccd_min%3A%2Ccd_max%3A1%2F18%2F2018&tbm=> <URL https://www.sigmaaldrich.com/catalog/product/sigma/40530?lang=en®ion=US> [retrieved on Jun. 16, 2020].

* cited by examiner

METHOD FOR USING AQUEOUS TWO-PHASE SYSTEM FOR THE ISOLATION, PURIFICATION AND/OR CONCENTRATION OF SHORT NUCLEIC ACID FRAGMENTS

CROSS-REFERENCE TO RELATED APPLICATIONS

This application is a divisional application of U.S. Ser. No. 16/646,582 filed on Mar. 12, 2020, which is the national stage of International Application No. PCT/US2018/051354 filed on Sep. 17, 2018, which claims the benefits of U.S. Ser. No. 62/560,180 filed on Sep. 18, 2017. The entire contents and disclosures of the preceding applications are incorporated by reference into this application.

FIELD OF THE INVENTION

This invention relates to a method for the isolation, concentration and/or purification of short nucleic acid fragments in an aqueous two-phase system (ATPS). In particular, the present invention provides a method, a kit and ATPS components for the isolation, concentration and/or purification of short nucleic acid fragments from biological materials. The present application cites various publications, the entire contents of which are incorporated herein by reference into this application.

BACKGROUND OF THE INVENTION

Since the discovery of polymerase chain reaction or simply PCR in 1983, whole genomes have been sequenced and numerous discoveries in the fundamental understanding of life sciences and key medical advances have been made possible because of it. Entire fields of technological innovations have been born for making PCR more efficient, more effective, and less costly. And because nucleic acids are both the inputs and the outputs of PCR, tireless efforts have been and are continuing to be expended to make their upstream preparation and downstream analysis more accurate, precise, rapid, and cost-effective.

The marginal gain for efficiency is hitting a plateau with diminishing return of scale. This bottleneck is especially evident when the need to isolate small nucleic acid fragments under 250 base pair (bp) in length. One field in which the need to Isolate, purify, and concentrate small nucleic acid (NA) fragments is the recent advent in the field of liquid biopsy. Liquid biopsy is based on the capturing and amplification of cell free DNA (cfDNA), specifically circulating tumor DNA (ctDNA), thus obtaining early diagnosis of tumorigenesis or recurrence of cancer in patients who are in remission. Circulating tumor DNA (circulating tumor ctDNA) is a type of DNA fragment derived from the tumor cells having the size of between 100-300 base pair. Circulating free DNA (cfDNA) released by tumor cells preserves the characteristics of the issue of origin. Analyzing and studying the cfDNA allow the genetic characterization of the tumor by a non-invasive process compared to the conventional biopsy. cfDNA analysis is a noninvasive and rapid alternative method of detecting and monitoring genomic alternations throughout the course of disease. The available techniques allow DNA extraction from cells/tissues of different origins. Different protocols can be used, commercialized as "kits" which can be used to extract nucleic acids from different materials (biological fluids, cell cultures, fresh or frozen tissue samples). cfDNA concentration is usually very low and cfDNA is highly fragmented with short peak fragment (e.g. smaller than 250 bp). In particular, nucleic acids of about 160-165 bp usually appear in urine which is a more desirable sample type for liquid biopsy. Thus the extraction method for the isolation of cfDNA from biological samples can significantly affect the yield of cfDNA which may further affect characteristics of different tests and degrees of clinical validation.

The challenge here is to isolate, purify, and concentrate the very rare and sparse nucleic acid fragments against a complex background of biological matrix. Often times the yield of relevant fragments is so low that subsequent PCR results may not have sufficient diagnostic sensitivity and specificity. Therefore, it is of utmost urgency that a new and more effective method of isolation, purification, and concentration of nucleic acid fragments smaller than 250 bp to be developed.

A variety of different methods have been developed for the isolation of nucleic acids from biological samples, for example, methods that involve selective adsorption of nucleic acids to a substrate, and methods that involve removal of contaminants from soluble nucleic acids. Presently available purification methods are based on the use of phenol/chloroform, salting out, the use of chaotropic salts and silica resins, the use of affinity resins, ion exchange chromatography and the use of magnetic beads as described in U.S. Pat. Nos. 5,057,426, 4,923,978, EP Patents 0512767 A1 and EP 0515484B and WO 95/13368, WO 97/10331 and WO 96/18731.

There are also known processes for purifying plasmid DNA by the aqueous two-phase system (ATPS) which is described in WO2004/106516 and Purification of plasmid DNA vectors by aqueous two-phase extraction and hydrophobic interaction chromatography, Journal of Chromatography A, 1082 (2005), 176-184. Both of the processes disclosed the use of ATPS for the plasmid DNA purification but none of them were designed for isolating nucleic acid with a length of 250 bp or below. It is not expected that existing processes for purifying large nucleic acid molecule is able to purify short nucleic acids of 250 bp or less with sufficient purity for satisfactory performance of downstream applications.

The need for preparing biological samples specifically for isolating, purifying, and concentrating nucleic acid fragments of 250 bp or smaller is very significant in both the arena of research and industry, but this need is largely unmet by existing methods. Although various methods of using different chemical formulations to achieve species separation in aqueous systems have been described, no successfully attempt has been taken to use such possibilities for the isolation, purification and concentration of nucleic acid fragments of 250 bp or smaller in a time-efficient, cost-effective, simple, rapid manner that also delivers superior yields, which the present invention has demonstrated to have achieved.

SUMMARY OF THE INVENTION

The present invention relates to the isolation, concentration and/or purification of short nucleic acid fragments in an aqueous two-phase system (ATPS). In one embodiment, the present invention provides a method of using an ATPS for the isolation, concentration and/or purification of short nucleic acid fragments having about or less than 250 base pairs (bp). In one embodiment, the present invention provides a composition and kit for the purification of short nucleic acid fragments having about or less than 250 base pairs from nucleic acid-containing biological materials. In another embodiment, the present invention provides a use of certain salts and/or polymers in an ATPS for the purification of short nucleic acid fragments having about or less than 250 base pairs from nucleic acid containing—biological materials.

BRIEF DESCRIPTION OF THE DRAWING

FIG. 1B shows a typical scenario in which the target molecule was concentrated in the bottom phase (shown in darker color).

DETAILED DESCRIPTION OF THE INVENTION

In the following description, several embodiments of the invention are described. For purposes of explanation, specific configurations and details are set forth in order to provide a thorough understanding of the embodiments. In addition, to the plural or singular forms of a word and to the extent that orientations of the embodiments are described as, "top", "bottom", "front", "back". "left", "right" and the like. These wordings are to aid the reader in understanding the embodiments and are not meant to be limiting physically. It is apparent to a person skilled in the art that the present invention may be practiced without specific details. The invention will be better understood by reference to the examples which follow, but those skilled in the art will readily appreciate that the specific examples are for illustrative purposes only and should not limit the scope of the invention which is defined by the claims which follow thereafter. It is to be noted that the transitional term "comprising" or "including", which is synonymous with "containing" or "characterized by", is inclusive or open-ended and does not exclude additional, unrecited elements or method steps.

In the present invention, an aqueous two-phase system (ATPS) has been adapted for the isolation, concentration and/or purification of short nucleic acid fragments having about or less than 250 base pairs (bp) from various biological materials.

In one embodiment, the present invention provides a method of using an aqueous two-phase system (ATPS) for the isolation, concentration and/or purification of short nucleic acid fragments having about or less than 250 base pairs (bp). In one embodiment, the method comprises the steps of (a) providing an ATPS composition; and
(b) contacting or mixing said ATPS composition with a sample solution comprising the short nucleic acid fragments,
(c) allowing a mixture of said ATPS and the sample solution to separate into a first phase and a second phase, wherein the short nucleic acid fragments partition into the first phase solution or the second phase solution, thereby isolating and concentrating the short nucleic acid fragments.

In one embodiment, the present invention provides a composition for isolating and concentrating nucleic acid fragments of 250 bp or less from a sample, the composition comprises a first phase component and a second phase component capable of forming an aqueous two phase system (ATPS) when the components are dissolved in an aqueous solution. In one embodiment, the first phase component is one or more of polymer, salt or micellar solution. In one embodiment, the second phase is one or more of polymer, salt or micellar solution. In one embodiment, the first phase component is a polymer and the second phase is a salt. In one embodiment, the nucleic acid fragments of 250 bp or less are concentrated in one phase.

In one embodiment, the present invention provides a method for isolating and concentrating nucleic acid fragments of 250 bp or less from a sample, the method mixes a composition described herein with a sample solution comprising the short nucleic acid fragments, thereby isolating and concentrating the short nucleic acid fragments.

In one embodiment, the short nucleic acid fragments are coding DNA, non-coding DNA, messenger RNA, ribosomal RNA, micro-RNA or transfer RNA. In one embodiment, the short nucleic acid fragments are cell-free DNA or circulating tumor DNA.

ATPS (Aqueous Two-Phase System)

Similar to an oil-water system, an ATPS consists of two distinct liquid phases, the ratios of which can easily be controlled. Biomolecules suspended in the ATPS system partition into one of the two aqueous phases based on their physicochemical properties (e.g., hydrophilicity and interfacial tension of the two phases), thereby concentrating the biomolecules of interest.

In one embodiment, the present invention provides a two-component Aqueous Two-Phase System (ATPS) for isolating/concentrating/purifying/recovering one or more short nucleic acid fragments or target molecules (e.g. a nucleic acid molecule) from a sample. Different molecules in a mixture would be distributed differentially between the two phases due to their different properties, and it is possible to separate and concentrate target molecules using ATPS with minimal set up and human intervention. In one embodiment, no power or equipment is necessary to bring about the phase separation, as the fluid flow relies purely on capillary action which is based on isothermal-dynamic principles.

The advantage of this invention is that high purity and concentration of the target molecule can be obtained in a simple way and compatible with downstream applications including but not limited to amplification (e.g. by PCR), sequencing, labeling or detection (e.g. by hybridization or Lateral-Flow Immunoassay (LFA)) without further step of purification or concentration.

The methods and devices provided herein are robust, inexpensive, simple, easy to handle, safe, user friendly and fast. The present method is able to purify and concentrate one or more short nucleic acid fragments or target molecules and thereby ensures the performance of the downstream applications using the purified and concentrated molecule will not be affected by impurities in the original sample.

Because of the unique features described herein, the present invention can purify and concentrate the target molecule conveniently and rapidly without the use of complex instrumentation, and is applicable to samples containing the one or more short nucleic acid fragments or target molecules in a very low amount, or of a small volume. Furthermore, the present method is readily adaptable to automation including high throughput screening systems.

Use of ATPS (Aqueous Two-Phase System) for Isolating and/or Concentrating Small Fragments of Nucleic Acids In one embodiment, the present invention is used to isolate, purify, recover and concentrate one or more short nucleic acid fragments or target molecules from a sample. In one embodiment, the present invention is able to separate the one or more short nucleic acid fragments or target molecules from non-target molecules, and concentrate the target nucleic acid molecules simultaneously.

In one embodiment of the present invention, the short nucleic acid fragments or target molecules are retained on the ATPS-embedded porous material while non-target materials are left in the liquid system (i.e., original sample plus any non-ATPS components). In one embodiment, the non-target materials are retained on the ATPS-embedded porous material while the short nucleic acid fragments or target molecules are left in the liquid system (i.e., original sample plus any non-ATPS components).

In the present invention, aqueous two-phase system (ATPS) has been adapted for the isolation, concentration and/or purification of short nucleic acid fragments having about or less than 250 base pairs from various biological materials.

In one embodiment, the present invention provides a method of using an aqueous two-phase system (ATPS) for the isolation, concentration and/or purification of short nucleic acid fragments having about or less than 250 base pairs. In one embodiment, the method comprises the steps of (a) providing an ATPS composition comprising a first phase solution and a second phase solution; and (b) contacting said ATPS composition with a sample solution comprising the short nucleic acid fragments, and allowing the short nucleic acid fragments to concentrate in the first phase solution or the second phase solution, thereby isolating, concentrating and/or purifying the short nucleic acid fragments.

In one embodiment, the ATPS composition is a mixed phase solution of ATPS components comprising polymers, salts and surfactants. In one embodiment, the composition separates into the first phase solution and the second phase solution after it is contacted with the sample solution, thereby initiates a phase separation.

In one embodiment, the nucleic acids are cell-free DNA (cfDNA). As used herein, "cell-free DNA" (cfDNA) is DNA that is present outside a cell, e.g., DNA present in the blood, plasma, serum, or urine of a subject. Without being bound by any particular theory or mechanism, it is believed that cfDNA is released or originated from cells, e.g., via apoptosis of the cells. As used herein, "native cfDNA" or "cfDNA of the subject" refers to cell-free DNA released or originated from cells (e.g., non-cancerous cells) of the subject. As used herein, "non-native cdDNA" or "cfDNA not native to the subject" refers to cell-free DNA from a non-native source that differs from the cfDNA of the subject in terms of sequence, e.g., a difference in sequence identity at one or more loci including but not limiting to those described herein. Examples of non-native DNA include, but are not limited to, transplant donor DNA and cancer/tumor DNA. Examples of non-native cdDNA include, but are not limited to, transplant donor cfDNA (also referred to herein as donor specific cfDNA) and tumor cfDNA (also referred to herein as cancer-specific cf-DNA). The source of non-native cf-DNA depends upon the subject. As another example, non-native cfDNA includes bacterial, fungal and viral DNA. For example, if a subject is a transplant recipient, non-native cDNA may be shed from the donated transplanted organ (donor specific cfDNA) and native cfDNA may be shed by cells from the host/subject (host cf-DNA). If the subject has cancer, non-native cf-DNA may be shed, e.g., by a tumor and/or metastasis (cancer-specific cf-DNA), and native cf-DNA may be shed, e.g., by noncancerous cells of the subject.

In one embodiment, the nucleic acids are circulating tumor DNA (ctDNA) that are present in the plasma or serum of cancer patients In one embodiment, short nucleic acid fragments subject to the present invention are equal to or smaller than 250 bp in size. In another embodiment, the short nucleic acid fragments are 160-165 bp in size. In another embodiment, the short nucleic acid fragments are about 20, 30, 40, 50, 60, 70, 80, 90, 100, 110, 120, 130, 140, 150, 160, 170, 180, 190, 200, 210, 220, 230, 240 or 250 bp in size.

In one embodiment, the short nucleic acid fragments are partitioned into the first phase solution. In another embodiment, the short nucleic acid fragments are partitioned into the second phase. In another embodiment, the short nucleic acid fragments are partitioned into the interface of the first phase solution and the second phase solution.

In one embodiment, the sample solution is a nucleic acid-containing sample or nucleic acid-containing biological material. The significance of the present invention is in the treatment and preparation of nucleic acids-containing samples and nucleic acid-containing biological materials, which include but not limited to tissues, blood, plasma, serum, cerebrospinal fluid (CSF), urine, saliva, fecal matters, and discharges such as tears, sputum, nasopharyngeal mucus, vaginal discharge, penile discharge.

Various ATPS systems that can be used in various embodiments of the present invention includes, but are not limited to, polymer-salt (e.g. PEG-salt), polymer-polymer (e.g. PEG-dextran, PEG-polyacrylate), micellar (e.g. Triton X-114), salt-micellar (e.g. salt-Triton X-114) or polymer-micellar (e.g. PEG-Triton X-114).

In one embodiment, the first and/or second phase solution comprises a polymer. In one embodiment, the polymer includes, but is not limited to, polyalkylene glycols, such as hydrophobically modified polyalkylene glycols, poly(oxyalkylene)polymers, poly(oxyalkylene)copolymers, such as hydrophobically modified poly(oxyalkylene)copolymers, polyvinyl pyrrolidone, polyvinyl alcohol (PVA), polyvinyl caprolactam, polyvinyl methylether, alkoxylated surfactants, alkoxylated starches, alkoxylated cellulose, alkyl hydroxyalkyl cellulose, silicone-modified polyethers, and poly N-isopropylacrylamide and copolymers thereof. In another embodiment, the first polymer comprises polyethylene glycol, polypropylene glycol, polyacrylate or dextran. In one embodiment, the polymer is UCON™ polymer (Dow Chemical Company) or Ficoll™ polymer (Sigma-Aldrich).

In one embodiment, the polymer concentration of the first phase solution or second phase solution is in the range of about 0.01% to about 90% by weight of the total weight of the aqueous solution (w/w). In various embodiments, the polymer solution is selected from a polymer solution that is about 0.01% w/w, about 0.05% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9% w/w, about 0.95% w/w, or about 1% w/w. In some embodiments, the polymer solution is selected from polymer solution that is about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, about 40% w/w, about 41% w/w, about 42% w/w, about 43% w/w, about 44% w/w, about 45% w/w, about 46% w/w, about 47% w/w, about 48% w/w, about 49% w/w, and about 50% w/w. In one embodiment, the concentration of polymer is about 0.01% to 40% w/w. In one embodiment, the concentration of polymer is about 6% to 35% w/w. In one embodiment, the concentration of polymer is about 10% to 30% w/w.

In one embodiment, the first and/or second phase solution comprises a salt and thereby forms a salt solution. In one embodiment, the salt subject to the present invention includes but is not limited to kosmotropic salts, chaotropic salts, inorganic salts containing cations such as straight or branched trimethyl ammonium, triethyl ammonium, tripropyl ammonium, tributyl ammonium, tetramethyl ammonium, tetraethyl ammonium, tetrapropyl ammonium and tetrabutyl ammonium, and anions such as phosphates, sulphate, nitrate, chloride and hydrogen carbonate. In another embodiment, the salt can be NaCl, $Na_3PO_4$, $NaH_2PO_4$, $Na_2HPO_4$, K $PO_4$, $KH_2PO_4$, $K_2HPO_4$, $Na_2SO_4$, $NaHSO_4$, potassium citrate, $(NHA)_2SO_4$, sodium citrate, sodium acetate or combinations thereof. Other salts, e.g. ammonium acetate, may also be used. In one embodiment, two or more salts are used for adjusting the pH value or altering the interfacial tension between the phases.

In one embodiment, the total salt concentration is in the range of about 0.01% to about 90%. A skilled person in the art will understand that the amount of salt needed to form an aqueous two-phase system will be influenced by molecular weight, concentration and physical status of the polymer.

In various embodiments, the salt solution is about 0.001% to 90% w/w. In various embodiments, the salt solution is about 0.01% w/w, about 0.05% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9% w/w, about 0.95% w/w, or about 1% w/w. In some embodiments, the salt solution is about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, about 40% w/w, about 41% w/w, about 42% w/w, about 43% w/w, about 44% w/w, about 45% w/w, about 46% w/w, about 47% w/w, about 48% w/w, about 49% w/w, and about 50% w/w. In one embodiment, the concentration of salt is about 2% to 40% w/w. In one embodiment, the concentration of salt is about 3% to 30% w/w. In one embodiment, the concentration of salt is about 5% to 20% w/w.

In one embodiment, the first phase solution and/or the second phase solution comprises a solvent that is immiscible with water. In some embodiments, the solvent comprises a non-polar organic solvent. In some embodiments, the solvent comprises an oil. In some embodiments, the solvent can be pentane, cyclopentane, benzene, 1,4-dioxane, diethyl ether, dichloromethane, chloroform, toluene or hexane.

In one embodiment, the first phase solution and/or second phase solution comprises a micellar solution. In some embodiments, the micellar solution comprises a nonionic surfactant. In some embodiments, the micellar solution comprises a detergent. In some embodiments, the micellar solution comprises Triton-X. In some embodiments, the micellar solution comprises a polymer similar to Triton-X, such as Igepal CA-630 and Nonidet P-40. In some embodiments, the micellar solution comprises essentially of Triton-X.

In one embodiment, the first phase solution comprises a micellar solution and the second phase solution comprises a polymer. In one embodiment, the second phase solution comprises a micellar solution and the first phase solution comprises a polymer. In one embodiment, the first phase solution comprises a micellar solution and the second phase solution comprises a salt. In one embodiment, the second phase solution comprises a micellar solution and the first phase solution comprises a salt. In one embodiment, the micellar solution is a Triton-X solution. In one embodiment, the first phase solution comprises a first polymer and the second phase solution comprises a second polymer. In one embodiment, the first/second polymer is selected from polyethylene glycol and dextran. In one embodiments, the first phase solution comprises a polymer and the second phase solution comprises a salt. In one embodiment, the second phase solution comprises a polymer and the first phase solution comprises a salt. In some embodiments, the first phase solution comprises polyethylene glycol and the second phase solution comprises potassium phosphate. In some embodiments, the second phase solution comprises polyethylene glycol and the first phase solution comprises potassium phosphate. In one embodiment, the first phase solution comprises a salt and the second phase solution comprises a salt. In one embodiment, the first phase solution comprises a kosmotropic salt and the second phase solution comprises a chaotropic salt. In some embodiments, the second phase solution comprises a kosmotropic salt and the first phase solution comprises a chaotropic salt.

In one embodiment, ratios of the first phase solution to the second phase solution are in the range of 1:1 to 1:1000. In some embodiments, the ratio of the first phase solution to the second phase solution can be a ratio of about 1:1, about 1:2, about 1:3, about 1:4, about 1:5, about 1:6, about 1:7, about 1:8, about 1:9, and about 1:10. In some embodiments the ratio of the first phase solution to the second phase solution can be a ratio of about 1-20, about 1:30, about 1:40, about 1:50, about 1:60, about 1:70, about 1:80, about 1:90, and about 1:100. In some embodiments the ratio of the first phase solution to the second phase solution is about 1:200, about 1:300, about 1:400, about 1:500, about 1:600, about 1:700, about 1:800, about 1:900, and about 1:1000.

In one embodiment, the ratio of the second phase solution to the first phase solution is about 1:1, about 1:2, about 1:3, about 1:4, about 1:5, about 1:6, about 1:7, about 1:8, about 1-9, or about 1:10. In some embodiments the ratio of the second phase solution to the first phase solution is about 1:20, about 1:30, about 1:40, about 1:50, about 1:60, about 1:70, about 1:80, about 1:90, or about 1:100. In some embodiments the ratio of the second phase solution to the first phase solution is about 1-200, about 1:300, about 1:400, about 1:500, about 1:600, about 1:700, about 1:800, about 1:900, or about 1:1000.

In one embodiment where the first phase solution and the second phase solution of the ATPS are polymer, after the phase separation of the mixture of the ATPS and sample, the polymer concentration of the first phase solution or second phase solution is in the range of about 0.01% to about 90% by weight of the total weight of the aqueous solution (w/w). In various embodiments, the concentration is about 0.01% w/w, about 0.05% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9% w/w, about 0.95% w/w, or about 1% w/w. In some embodiments, the salt solution is selected from polymer solution that is about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, about 40% w/w, about 41% w/w, about 42% w/w, about 43% w/w, about 44% w/w, about 45% w/w, about 46% w/w, about 47% w/w, about 48% w/w, about 49% w/w, and about 50% w/w. In one embodiment, the polymer concentration in the first phase solution is about 10% to 50% w/w while the concentration in the second phase solution is about 0.01% to 6% w/w. In another embodiment, the polymer concentration in the first phase solution is about 22% to 45% w/w while the concentration in the other phase is about 0.01% to 4% w/w.

In various embodiments where the first phase solution and the second phase solution of the ATPS are salt, after the phase separation of the mixture of the ATPS and sample, the salt concentration of the first phase solution or second phase solution is about 0.001% to 90% w/w. In various embodiments, the salt concentration is about 0.01% w/w, about 0.05% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9% w/w, about 0.95% w/w, or about 1% w/w. In some embodiments, the salt solution is selected from polymer solution that is about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, about 40% w/w, about 41% w/w, about 42% w/w, about 43% w/w, about 44% w/w, about 45% w/w, about 46% w/w, about 47% w/w, about 48% w/w, about 49% w/w, and about 50% w/w. In one embodiment, the concentration of salt in the first phase is about 0.01% to 10% w/w and the concentration of salt in second phase is about 20% to 40% w/w. In another embodiment, the concentration of salt in the first phase is about 0.01% to 6% w/w and the concentration of salt in the second phase is about 22% to 35% w/w.

In one embodiment, the present invention provides a composition for isolating and/or concentrating short nucleic acid fragments, the composition comprises components that are capable of forming an Aqueous Two-Phase System (ATPS).

In one embodiment, the present composition comprises a mixed phase solution comprising a first phase solution and a second phase solution, including those described in the preceding description.

In one embodiment, the present composition for isolating and/or concentrating short nucleic acid fragments comprises polyethylene glycol (PEG) 6000 and potassium phosphate dibasic ($K_2HPO_4$). In one embodiment, the present composition for isolating and/or concentrating short nucleic acid fragments comprises about 5-20% polyethylene glycol (PEG) 6000 and 5-35% $K_2HPO_4$. In another embodiment, the present composition for isolating and/or concentrating short nucleic acid fragments comprises 8% polyethylene glycol (PEG) 6000 and 22% $K_2HPO_4$.

In one embodiment, the present composition for isolating and/or concentrating short nucleic acid fragments comprises polyethylene glycol (PEG) 1000 and $K_2HPO_4$. In one embodiment, the present composition for isolating and/or concentrating short nucleic acid fragments comprises about 10-30% polyethylene glycol (PEG) 1000 and 5-20% $K_2HPO_4$. In another embodiment, the present composition for isolating and/or concentrating short nucleic acid fragments comprises 15% polyethylene glycol (PEG) 1000 and 15% $K_2HPO_4$.

In one embodiment, the present composition for isolating and/or concentrating short nucleic acid fragments comprises polyethylene glycol (PEG) 1000 and a mixture of potassium phosphate dibasic ($K_2HPO_4$) and potassium phosphate monobasic ($KH_2PO_4$).

Adjustment of Concentration Factors

By way of illustration, in some embodiments, the target short nucleic acid fragments are concentrated by 10-fold in the first phase solution, e.g., by using a 1:9 volume ratio of first phase solution to second phase solution.

In one embodiment, the relative amounts of ATPS components can be changed. The volume ratio of the two components of ATPS are controlled so as to isolate/purify/concentrate/recover the short nucleic acid fragments or target molecules preferentially in one phase.

To better quantify the phenomena associated with the present invention, an assay was developed to evaluate the correlation between the relative amounts of ATPS components and the achieved outcome (e.g., efficiency of concentration/isolation/recovery). With this, the concentration factor, isolation efficiency and recovery rate can be selected and fine-tuned by adjusting the relative amount of the ATPS components.

Figure 1A:
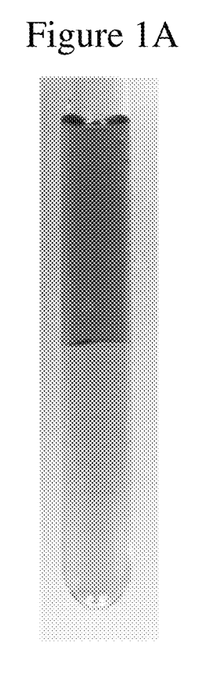
FIGS. 1A and 1B show phase separation induced by the addition of polymer and salt. The tube in FIG. 1A consists of two separated phases with a top/bottom phase volume ratio of 1:1. The tube in FIG. 1B shows two separated phases with a top/bottom phase volume ratio of 9:1. By adjusting ATPS components, the volume ratio of top phase to bottom phase can be changed from 1:1 to 9:1, and can be further altered to concentrate a target molecule into the phase with a smaller volume.
Figure 1B:
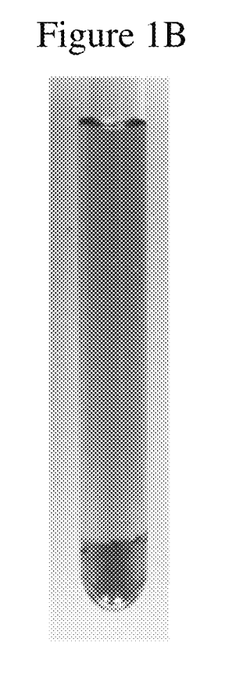
Figure 2:
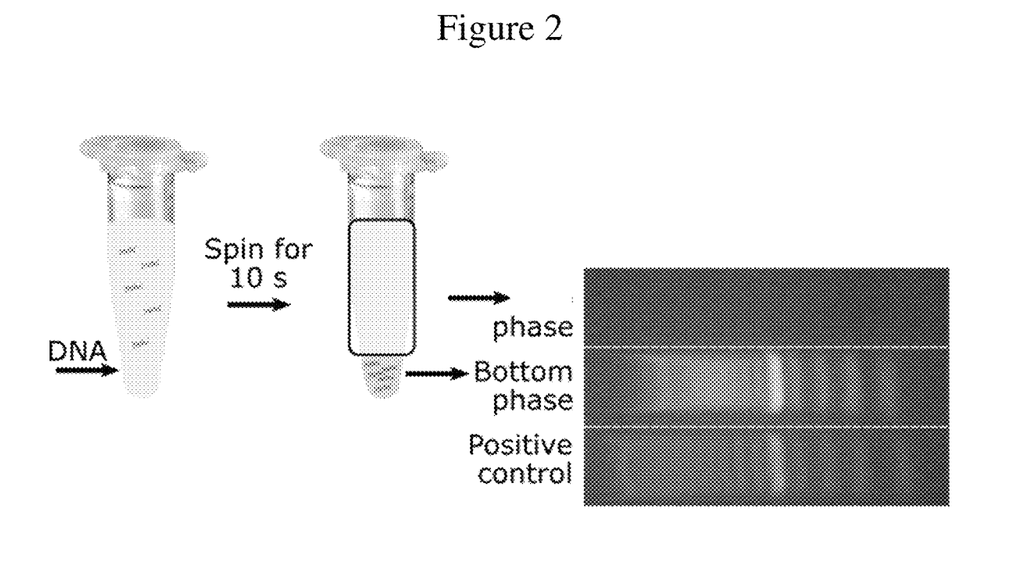
FIG. 2 shows a gel electrophoresis image of DNA purified by one embodiment of the present invention.

In one embodiment, the ratio between the two phases in an ATPS can be easily controlled by varying concentrations of ATPS components. FIGS. 1A-B show phase separation concentration induced by the addition of different ATPS components (e.g. polymer and salt) to the solution. ATPS components and sample were mixed 1:1. By adjusting ATPS components, the mixture phase separates and the target molecules partition into one of the two phases. FIG. 1B shows that the target molecule was concentrated in the bottom phase with a 9:1 volume ratio. The volume ratio of top phase to bottom phase can be further altered to concentrate the target molecule in a phase with a smaller volume.

In another embodiment, by adjusting the ATPS components (for example, adding additional ATPS component(s) of the same or different types to the mixture, or altering the relative volume or concentration of ATPS components to be added to the mixture when preparing the final solution, or adjusting the volume of sample solution to be added to the system when preparing the final solution), the relative volume or concentration of ATPS components in the final mixture can be altered. In one embodiment, the volume ratio of top phase to bottom phase can be changed from 1:1 to 9:1, or higher ratios. This phenomenon can be leveraged to concentrate a target molecule without the need for power, equipment, or training. In a simple medium, such as water or a saline solution, this is trivial to reproduce; however, given a complex medium (e.g. saliva, blood, urine, plasma, serum, cerebrospinal fluid (CSF), fecal matters, and discharges such as tears, sputum, nasopharyngeal mucus, vaginal discharge and penile discharge) that has high variability and potentially other interfering substances, it is more difficult to achieve a useful volume ratio. Removing interfering substances from the complex medium may help.
For example, citric acid can be used to remove urea from urine, or trichloroacetic acid can be used to remove protein from saliva in some embodiments of this invention.

Design of ATPS-Embedded Porous Material

In one embodiment, the present method provides a porous material embedded with ATPS components. In one embodiment, the short nucleic acid fragments can be isolated and concentrated as the sample travels through the porous material embedded with ATPS components. In one embodiment, the isolated and concentrated short nucleic acid fragments are collected from the porous material directly for subsequent analysis or storage.

Porous material may be made of any suitable porous material which can absorb and transfer liquid. Suitable porous materials for this invention include but are not limited to fiberglass paper, cotton-based paper, other types of paper, polymer foams, cellulose foams, other types of foams, rayon fabric, cotton fabric, other types of fabric, wood, stones, and any other materials that can absorb and transfer liquid.

In one embodiment, the ATPS comprises a mixed phase solution comprising a first phase solution and a second phase solution, wherein components of the first phase solution and components of the second phase solution are embedded in said porous material at a concentration or a loading that is sufficient to undergo a phase separation as the mixed phase solution flows through the porous material.

In one embodiment, the ATPS components are embedded in said porous material at a concentration or a loading that is sufficient to undergo a phase separation as the mixed phase solution flows through the porous material.

In one embodiment, some of the ATPS components are embedded in the porous material and then dehydrated prior to the addition of a sample containing the target nucleic acid fragments to said porous material.

In one embodiment, some of the ATPS components are embedded in the porous material and then dehydrated (the "pre-treated porous material"), while the remaining ATPS components are first mixed with a sample containing the target nucleic acid fragments and then subject to subsequent isolation and concentration through phase separation within the pre-treated porous material.

In one embodiment, some ATPS components are first mixed with a sample containing the short nucleic acid fragments, the resulting mixture is then embedded in the porous material; the remaining ATPS components are then added to the porous material for subsequent isolation/concentration through phase separation within the porous material.

In one embodiment, the short nucleic acid fragments are in contact with the mixture of ATPS components or mixed with ATPS components, and partitions into the first phase solution, the second phase solution or the interface (or interphase) between the first phase solution and the second phase solution as it travels through the porous material.

In one embodiment, there is provided a two-component ATPS (aqueous two-phase system) within a porous material for separating short nucleic acid fragments and long nucleic acid molecules in a sample. In one embodiment, the short nucleic acid fragments and the long nucleic acid molecules partition into different phases of the ATPS as the ATPS undergoes phase separation within the porous material.

In one embodiment, the porous material and ATPS are selected so that the first phase solution flows through the porous matrix at a first rate and the second phase solution flows through the porous matrix at a second rate, wherein the first rate and the second rate are different.

In one embodiment, the porous material is commercially available or manufactured in-house.

In one embodiment, to integrate the ATPS components into the porous material, the ATPS components are solubilized in water (or appropriate buffer) and applied on the porous material in certain ratios and/or concentrations. The porous materials are then placed in a lyophilizer to remove water, resulting in the embedment of ATPS components directly on the porous material. Upon introduction of the sample to the porous materials, the ATPS components instantly undergo rehydration and thereby separate the short nucleic acid fragments or target molecules in the sample. In one embodiment, the short nucleic acid fragments are concentrated at the front of the fluid flow. In one embodiment, no external power or equipment is used to provide a driving force.

Improved Diagnostic Using the Lateral-Flow Immunoassay (LFA)

The short nucleic acid fragments obtained by the present method can be subject to detection or analysis using Lateral-Flow Immunoassay (LFA).

Lateral flow immunoassay (LFA) methods and devices have been described extensively. See, e.g., Gordon and Pugh, U.S. Pat. No. 4,956,302; H. Buck, et al., WO 90/06511; T. Wang. U.S. Pat. No. 6,764,825; W. Brown, et al., U.S. Pat. No. 5,008,080; Kuo and Meritt, U.S. Pat. No. 6,183,972, EP 00987551 A3. Such assays involve the detection and determination of an analyte substance that is a member of a specific binding pair consisting of a ligand and a receptor. The ligand and the receptor are related in that the receptor specifically binds to the ligand, being capable of distinguishing a specific ligand or ligands from other sample constituents having similar characteristics. Immunological assays involving reactions between antibodies and antigens are one such example of a specific binding assay. Other examples include DNA and RNA hybridization reactions and binding reactions involving hormones and other biological receptors.

In one embodiment, the present invention is capable of concentrating short nucleic acid fragments indicative of a disease present in a subject, the product obtained is subject to downstream diagnostic procedure requiring the detection or quantification of the short nucleic acid fragments. It is also expected that the present invention can reduce the signal-to-noise ratio and enhance the positive signal in Lateral-Flow Immunoassay (LFA) since the concentration of the short nucleic acid fragments have increased. False positive rate and false negative rate could also be lowered as a result. The concentration can be improved and therefore it is possible to detect molecules which could not be detected due to their low abundance or interference by impurities in the sample.

It may produce a false negative result if the short nucleic acid fragments has extremely low concentration. In one embodiment, due to the increased concentration of the short nucleic acid fragments, the detection limit of LFA is improved. As a result, the reproducibility of the test is increased.

In one embodiment, this invention provides a composition for isolating and concentrating nucleic acid fragments of 250 bp or less from a sample, the composition comprise a first phase component and a second phase component capable of forming an aqueous two phase system (ATPS) when the components are dissolved in an aqueous solution. In one embodiment, the first phase component is a polymer dissolving in a first phase at a concentration of 5-20 wt %, and the second phase component is a salt dissolving in a second phase at a concentration of 5-35 wt %, and when the nucleic acid fragments are mixed with the ATPS, the fragments are concentrated in one of the two phases.

In one embodiment of the present composition, the polymer is polyalkylene glycols, poly (oxy alkylene)polymers, poly(oxyakylene)copolymers, polyvinyl pyrrolidone, polyvinyl alcohol, polyvinyl caprolactam, polyvinyl methylether, alkoxylated surfactants, alkoxylated starches, alkoxylated cellulose, alkyl hydroxyalkyl cellulose, silicone-modified polyethers, poly N-isopropylacrylamide, polyethylene glycol, polypropylene glycol, polyacrylate, dextran, UCON™ polymer or Ficoll™ polymer.

In one embodiment of the present composition, the salt is kosmotropic salts, chaotropic salts, inorganic salts having a cation of trimethyl ammonium, triethyl ammonium, tripropyl ammonium, tributyl ammonium, tetramethyl ammonium, tetraethyl ammonium, tetrapropyl ammonium or tetrabutyl ammonium, and an anion of phosphate, sulphate, nitrate, chloride or hydrogen carbonate, sodium chloride, sodium phosphate, potassium phosphate, sodium sulphate, potassium citrate, ammonium sulfate, sodium citrate, sodium acetate or ammonium acetate.

In one embodiment of the present composition, the polymer is polyethylene glycol having a molecular weight ranges from 100 to 10,000 Da.

In one embodiment of the present composition, the salt is one or more of potassium phosphate dibasic, potassium phosphate monobasic, sodium chloride, sodium sulphate, and sodium phosphate.

In one embodiment of the present composition, when the sample is mixed with the composition, the resulting mixture undergoes phase separation and nucleic acid fragments of 250 bp or less are concentrated in one of the two phases. In one embodiment, nucleic acid fragments larger than 250 bp and fragments of 250 bp or less are concentrated in different phases of the ATPS.

In one embodiment of the present composition, the nucleic acid fragments are coding DNA, non-coding DNA, messenger RNA, ribosomal RNA, micro-RNA or transfer RNA. In one embodiment, the nucleic acid fragments are cell-free DNA or circulating tumor DNA.

In one embodiment of the present composition, the sample is blood, plasma, serum, cerebrospinal fluid, urine, saliva, fecal matter, tear, sputum, nasopharyngeal mucus, vaginal discharge or penile discharge.

In one embodiment, this invention provides a method for isolating and concentrating nucleic acid fragments of 250 bp or less from a sample, the method comprises:
  a) preparing a composition described in this application;
  b) mixing the composition from step a) with an aqueous solution containing the sample, allowing the resulting mixture to partition into two phases, and the nucleic acid fragments are concentrated in one of the two phases; and
  c) isolating the nucleic acid fragments from one of the two phases.

In one embodiment, this invention provides a method for isolating and concentrating nucleic acid fragments of 250 bp or less from a sample, the method comprises:
  a) preparing a composition comprising a first phase component and a second phase component capable of forming an aqueous two phase system (ATPS) when the components are dissolved in an aqueous solution, and the first phase component is a polymer dissolving in a first phase at a concentration of 5-20 wt %, and the second phase component is a salt dissolving in a second phase at a concentration of 15-25 wt %;
  b) mixing the composition from step a) with an aqueous solution containing the sample, allowing the resulting mixture to partition into two phases, and the nucleic acid fragments are concentrated in one of the two phases; and
  c) isolating one of the two phases that is concentrated with the nucleic acid fragments.

In one embodiment of the present method, the method further comprises recovering the nucleic acid fragments from the phase in step c).

In one embodiment of the present method, the polymer is polyalkylene glycols, poly (oxy alkylene)polymers, poly (oxyalkylene)copolymers, polyvinyl pyrrolidone, polyvinyl alcohol, polyvinyl caprolactam, polyvinyl methylether, alkoxylated surfactants, alkoxylated starches, alkoxylated cellulose, alkyl hydroxyalkyl cellulose, silicone-modified polyethers, poly N-isopropylacrylamide, polyethylene glycol, polypropylene glycol, polyacrylate dextran, UCON™ polymer or Ficoll™ polymer.

In one embodiment of the present method, the salt is kosmotropic salts, chaotropic salts, inorganic salts having a cation of trimethyl ammonium, triethyl ammonium, tripropyl ammonium, tributyl ammonium, tetramethyl ammonium, tetraethyl ammonium, tetrapropyl ammonium or tetrabutyl ammonium, and an anion of phosphate, sulphate, nitrate, chloride or hydrogen carbonate, sodium chloride, sodium phosphate, potassium phosphate, sodium sulphate, potassium citrate, ammonium sulfate, sodium citrate, sodium acetate or ammonium acetate.

In one embodiment of the present method, the polymer is polyethylene glycol having a molecular weight ranges from 100 to 10,000 Da.

In one embodiment of the present method, the salt is one or more of potassium phosphate dibasic, potassium phosphate monobasic, sodium chloride, sodium sulphate, and sodium phosphate.

In one embodiment of the present method, nucleic acid fragments larger than 250 bp and fragments of 250 bp or less are concentrated in different phases of the ATPS in step b).

In one embodiment of the present method, the nucleic acid fragments are coding DNA, non-coding DNA, messenger RNA, ribosomal RNA, micro-RNA or transfer RNA. In one embodiment, the nucleic acid fragments are cell-free DNA or circulating tumor DNA.

In one embodiment of the present method, the sample is blood, plasma, serum, cerebrospinal fluid, urine, saliva, fecal matter, tear, sputum, nasopharyngeal mucus, vaginal discharge or penile discharge.

In one embodiment of the present method, the nucleic acid fragments are concentrated by at least 10 folds as compared to the sample.

This invention will be better understood by reference to the examples which follow. However, one skilled in the art will readily appreciate that the examples provided are merely for illustrative purposes and are not meant to limit the scope of the invention which is defined by the claims following thereafter.

Throughout this application, it is to be noted that the transitional term "comprising", which is synonymous with "including", "containing" or "characterized by", is inclusive or open-ended, and does not exclude additional, un-recited elements or method steps.

EXAMPLES

Figure 3:
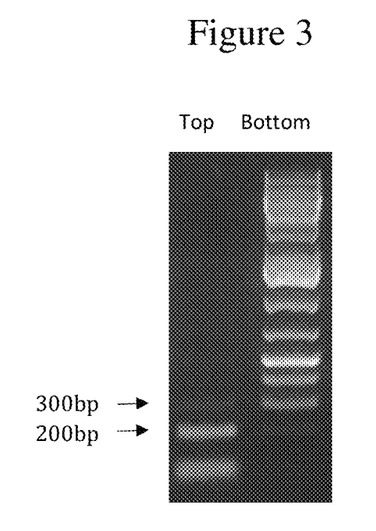
FIG. 3 shows a gel electrophoresis image of nucleic acids of different sizes partitioned into two different phases according to one embodiment of the present invention.

Example 1—Selective Isolation and Concentration of Short Nucleic Acid Fragments (<250 bp) from PBS Solution Using Aqueous Two-Phase System The DNA ladder (GeneRuler 1 kb plus DNA Ladder, Thermo Fisher Scientific) was spiked into 1 mL of aqueous two-phase system composed of 11% (w/w) polyethylene glycol (PEG) 6000 and 20% (w/w) $K_2HPO_4$ in PBS solution to make a final DNA concentration of 1 μg/mL. After vortexing thoroughly, the mixtures were centrifuged for 10 s at 10000 rcf for phase separation. The volume ratio of top phase to bottom phase was around 1:3. The top and bottom phases were extracted and transferred to new tubes respectively. The extracted phases were subjected to ethanol precipitation and the precipitates were separated by gel electrophoresis so as to visualize the DNA size partition in each phase, as shown in FIG. 3. Most of the nucleic acids larger than 250 bp partitioned into the bottom phase (right lane) while nucleic acids smaller than 250 bp partitioned into the top phase (left lane). Since the volume ratio of top phase to bottom phase was around 1:3, the shorter nucleic acid fragments were isolated from the longer nucleic acid fragments and subsequently concentrated into a smaller volume of solution.

The short nucleic acid fragments obtained from the above procedures were further analyzed by a LFA, with DNA sample without concentration by ATPS as a control. ImageJ or Gelanalyzer was used to measure the intensity of the test line and the results are summarized in below Table 1:

TABLE 1

| Intensity of test line | | |
|---|---|---|
| | DNA concentrated by ATPS | Control |
| Intensity of test line | 60x | 1x |

Example 2—Selective Isolation and Concentration of Short Nucleic Acid Fragments (<250 bp) from Plasma Sample Using Aqueous Two-Phase System The DNA ladder (GeneRuler Low Range DNA Ladder, Thermo Fisher Scientific) was spiked into 500 ul of plasma sample. The spiked plasma sample was added in to 500 ul of aqueous two-phase system composed of 15% (w/w) polyethylene glycol (PEG) 1000 and 15% (w/w) $K_2HPO_4$ in MilliQ water to make a final DNA concentration of 1 μg/mL. After vortexing thoroughly, the mixtures were centrifuged for 10 s at 10000 rcf for phase separation. The volume ratio of top phase to bottom phase was around 1:1.

The bottom phase was extracted and added into another ATPS solution composed of 11% (w/w) polyethylene glycol (PEG) 6000 and 20% (w/w) $K_2HPO_4$. After vortexing thoroughly, the mixtures were centrifuged for 10 s at 10000 rcf for phase separation. The volume ratio of top phase to bottom phase was around 1:3. The top and bottom phases were extracted and transferred to new tubes respectively. The extracted phases were subjected to ethanol precipitation and the precipitates were separated by gel electrophoresis so as to visualize the DNA size partition in each section (FIG. 3). Nucleic acids larger than 250 bp partition into bottom phase (right lane) while nucleic acids smaller than 250 bp partition into top phase (left lane), and therefore the smaller size of nucleic acids were isolated from the sample solution and concentrated into a smaller volume of solution.

Figure 4:
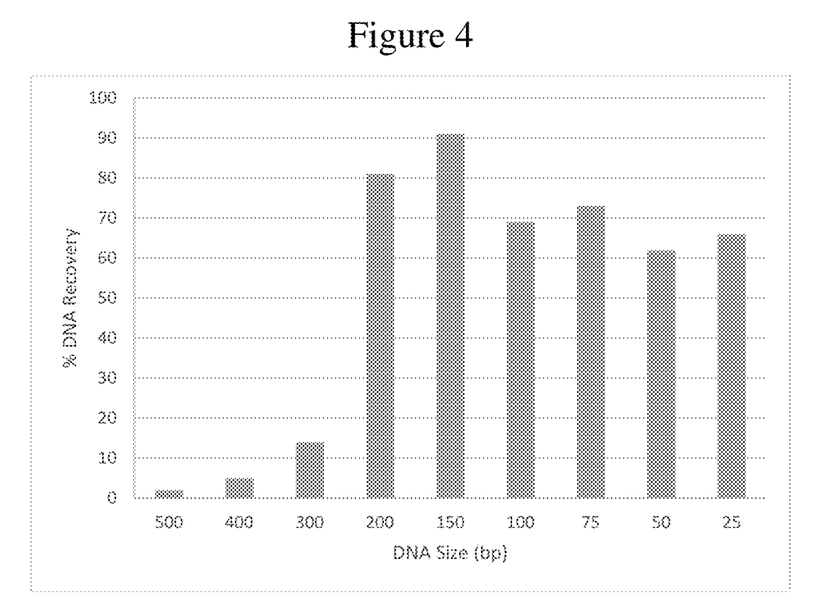
FIG. 4 shows the % recovery of DNA of different sizes extracted according to one embodiment of the present invention.

After isolation and concentration by the ATPS as described in this example, the recovery of different sizes of the DNA ladder were estimated (FIG. 4, wherein percentage of recovery=absolute yield of DNA recovered/amount of DNA spiked in the sample). It was found that DNA that were smaller than 250 bp were recovered in high percentage while DNA that were larger than 250 bp were significantly diminished. It demonstrated that the current invention is specific to capture DNA that were smaller than 250 bp.

Example 3—Comparison of the Aqueous Two-Phase System with the QIAamp Blood DNA Mini Kit (Qiagen)

Digested DNA plasmids of different sizes (250, 200, 150, 100, 75, 50, 25 bp) was spiked into plasma sample to make a final DNA concentration of 100 ng/mL, 1 mL of the resulting spiked plasma sample was added into 1 mL of aqueous two-phase system composed of 15% (w/w) polyethylene glycol (PEG) 1000 and 15% (w/w) $K_2HPO_4$ in MilliQ water. After vortexing thoroughly, the mixtures were centrifuged for 10 s at 10000 rcf for phase separation. The volume ratio of top phase to bottom phase was around 1:1.

The bottom phase was extracted and added into another ATPS solution composed of 8% (w/w) polyethylene glycol (PEG) 6000 and 22% (w/w) $K_2HPO_4$. After vortexing thoroughly, the mixtures were centrifuged for 10 s at 10000 rcf for phase separation. The volume ratio of top phase to bottom phase was around 1:5. The top phase was extracted and transferred to new tube.

Figure 5:
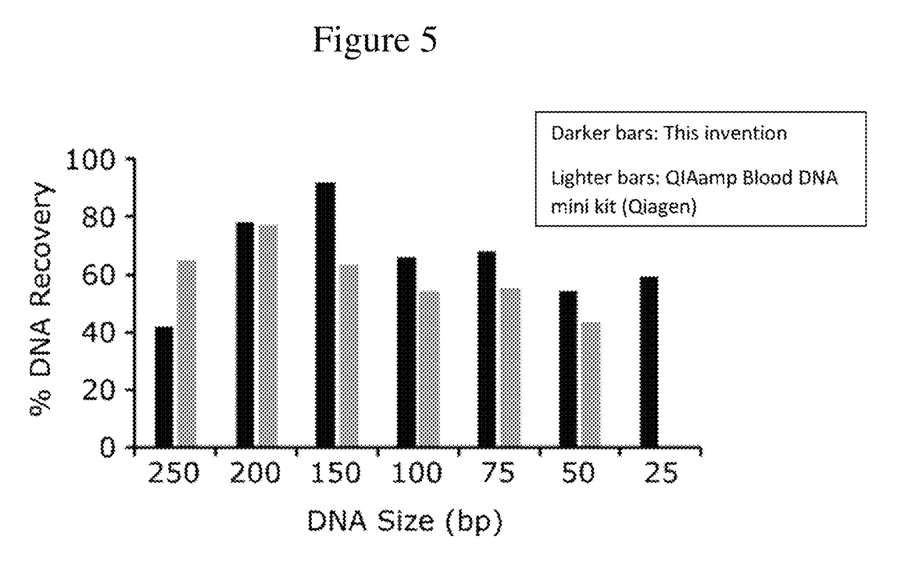
FIG. 5 compares the % recovery of DNA of different sizes extracted by one embodiment of the present invention and by the QIAamp Blood DNA mini kit.

Another extraction was conducted with 1 mL of the spiked plasma sample using QIAamp Blood DNA mini kit (Qiagen). The isolation effect on nucleic acids by using two different methods were compared by an electrophoretic assay of the isolated nucleic acids on the Agilent Bioanalyzer. The results were shown in FIG. 5. As shown in FIG. 5, when using the present invention, over 50-80% of nucleic acids that were shorter than 250 bp (25-200 bp) were extracted while about 80% of nucleic acids that were of 150-200 bp were extracted. In contrast, it was found that QIAamp Blood DNA mini Kit cannot extract any DNA of 25 bp. Therefore, the present invention showed an improved performance compared to QIAamp Blood DNA mini Kit.

What is claimed is:

1. A method for selectively isolating and concentrating nucleic acid fragments of 250 bp or less from a sample, comprising:
    a) preparing a composition comprising an aqueous solution, a first phase component and a second phase component capable of forming an aqueous two phase system (ATPS) when the components are dissolved in the aqueous solution such that a first phase solution and a second phase solution are formed, wherein the first phase component is a polymer to dissolve in the first phase at a concentration of 5-20 wt %, and the second phase component is a salt to dissolve in the second phase at a concentration of 15-25 wt %; wherein the polymer is polyethylene glycol having a molecular weight range from 1000 to 6000 Da, and the salt is potassium phosphate dibasic; wherein when the components are dissolved in the aqueous solution, the volume ratio of the first phase solution to the second phase solution is 1:1-1:5;
    b) mixing the composition from step a) with said sample, allowing the resulting mixture to partition into two phases, wherein said nucleic acid fragments are concentrated in one of the two phases; and
    c) isolating one of the two phases that is concentrated with said nucleic acid fragments of 250 bp or less.

2. The method of claim 1, further comprising recovering the nucleic acid fragments from the phase in step c).

3. The method of claim 1, wherein said polyethylene glycol is polyethylene glycol 6000, present in the weight concentration of 11% or 8%, and wherein the weight concentration of potassium phosphate dibasic is 20% or 22%.

4. The method of claim 1, further comprising the following steps before step b):
    i) preparing a composition comprising a third phase component and a fourth phase component forming a second aqueous two phase system (ATPS) when the components are dissolved in a second aqueous solution, wherein the third phase component comprises a polymer to dissolve in a third phase, and the fourth phase component comprises a salt to dissolve in a fourth phase, wherein the polymer is 10-30% polyethylene glycol (PEG) 1000 and the salt is 5-20% potassium phosphate dibasic;
    ii) mixing the composition from step i) with a sample solution comprising said nucleic acid fragments, allowing the resulting mixture to partition into two phases, wherein said nucleic acid fragments are concentrated in the bottom phase; and
    iii) isolating the bottom phase as said sample for step b).

5. The method of claim 1, wherein said nucleic acid fragments are selected from the group consisting of coding DNA, non-coding DNA, messenger RNA, ribosomal RNA, micro-RNA and transfer RNA.

6. The method of claim 1, wherein said nucleic acid fragments are cell-free DNA or circulating tumor DNA.

7. The method of claim 1, wherein the sample is selected from the group consisting of blood, plasma, serum, cerebrospinal fluid, urine, saliva, fecal matter, tear, sputum, nasopharyngeal mucus, vaginal discharge and penile discharge.

8. The method of claim 1, wherein said nucleic acid fragments are concentrated by at least 10 folds as compared to said sample.

9. The method of claim 3, wherein the weight concentration of said polyethylene glycol is 11% or 8% and wherein the weight concentration of said potassium phosphate dibasic is 20% or 22%.

10. The method of claim 3, wherein the weight concentration of said polyethylene glycol is 11% and wherein the weight concentration of said potassium phosphate dibasic is 20%.

11. The method of claim 3, wherein the weight concentration of said polyethylene glycol is 8%, and wherein the weight concentration of said potassium phosphate dibasic is 22%.

12. The method of claim 1, wherein said polyethylene glycol is polyethylene glycol 1000.

13. The method of claim 12, wherein the weight concentration of said polyethylene glycol is 15%, and the weight concentration of said potassium phosphate dibasic is 15%.

\* \* \* \* \*